United States Patent [19]

Ulmer

[11] Patent Number: 5,776,674

[45] Date of Patent: Jul. 7, 1998

[54] CHEMICAL BIOCHEMICAL AND BIOLOGICAL PROCESSING IN THIN FILMS

[75] Inventor: Kevin M. Ulmer, Cohasset, Mass.

[73] Assignee: SEQ, Ltd. Princeton, N.J.

[21] Appl. No.: 462,485

[22] Filed: Jun. 5, 1995

[51] Int. Cl.⁶ .......................... C12Q 1/68; G01N 33/53; G01N 33/543; C07H 21/04
[52] U.S. Cl. .......................... 435/6; 435/5; 435/91.1; 435/7.1; 435/7.2; 435/7.9; 436/172; 436/518; 436/527; 436/543; 436/547; 356/364; 536/24.3; 536/24.32; 536/24.33; 530/388.1; 530/333; 530/334
[58] Field of Search .......................... 435/6, 5, 172, 435/91.1, 7.1–7.9; 536/24.3–24.33; 436/518, 527, 543, 547; 356/364; 530/333, 334, 388.1

[56] References Cited

U.S. PATENT DOCUMENTS 5,079,169   1/1992   Chu et al. .......................... 436/172

OTHER PUBLICATIONS

Kuo and Sheetz, Science 260;232–234, 1995.

*Primary Examiner*—W. Gary Jones
*Assistant Examiner*—Dianne Rees
*Attorney, Agent, or Firm*—Pennie & Edmonds LLP

[57] ABSTRACT

An optical trap is used to translate a particle through a thin film coating on an optically-flat surface. Preferably, the thin film coating is heterogeneous and the optical trap is used to move the particle through a succession of different regions of the thin film coating where different chemical, biochemical and/or biological processes take place. Examples of chemical, biochemical and/or biological processes that might be implemented in accordance with the invention include the following: oligonucleotide synthesis and sequencing, peptide synthesis and sequencing, carbohydrate synthesis and sequencing, combinatorial library synthesis and screening, conventional (i.e., Sanger or Maxam-Gilbert) DNA sequengcing, or single-molecule DNA sequencing. In one embodiment of the invention, reaction products are left behind as the particle is moved through the thin film coating. Advantageously, these products can be identified by suitable means.

18 Claims, 9 Drawing Sheets

5,776,674

1

CHEMICAL BIOCHEMICAL AND BIOLOGICAL PROCESSING IN THIN FILMS

FIELD OF THE INVENTION

This application relates to chemical or biochemical processing in thin films. It relies on the use of devices such as an optical trap to move a particle relative to the thin film.

BACKGROUND OF THE INVENTION

An optical trap is a device in which a particle can be trapped near the focus of a strongly focused light beam such as a laser beam. The particle is held in the trap by the axial gradient force which is proportional to the gradient of the light intensity and points in the direction of increased intensity. In general, single-beam optical trapping can be achieved for particles having sizes ranging from about 10 µm to less than about 10 nm.

U.S. Pat. Nos. 4,893,886 and 5,079,169, which are incorporated herein by reference, describe optical traps that are used to translate trapped particles in liquid cells or films. This may be accomplished by trapping the particle in a laser beam and then moving the cell relative to the laser beam (Col. 3, lines 31–34 of the '886 patent) or moving the laser beam relative to the cell (Col. 4, lines 18–20 of the '886 patent; Col. 2, lines 35–40 of the '169 patent). The '886 patent describes the use of an optical trap to manipulate biological particles such as viruses, yeast, E. coli bacteria, blood cells and parts of cells (Col. 4, lines 45–49). The '169 patent describes the use of an optical trap to manipulate "polymer filaments" including nucleic acid fragments (Col. 1, lines 1–10).

Optical traps using multiple laser beams are described in Buican et al., 1989, SPIE: New Technologies in Cytometry, 1063:190–197; Tashiro et al., 1993, Optical Engineering 32(11):2812–2817, which are incorporated herein by reference.

Commercial examples of such optical trapping systems using such technology include the LaserTweezers™ 2000 from Cell Robotics, Inc., Albuquerque, N. Mex.; the Compact Photonic Tweezers from S+L GmbH, Heidelberg, Germany; and the PALM® Laser-Microscope System from P.A.L.M. GmbH, Wolfratshausen, Germany.

SUMMARY OF THE INVENTION

In a preferred embodiment of the present invention, an optical trap is used to translate a particle through a thin film coating on an optically-flat surface. Preferably, the thin film coating is heterogeneous and the optical trap is used to move the particle through a succession of different regions of the thin film coating where different chemical, biochemical and/or biological processes take place. Examples of chemical, biochemical and/or biological processes that might be implemented in accordance with the invention include the following: oligonucleotide synthesis and sequencing, peptide synthesis and sequencing, carbohydrate synthesis and sequencing, combinatorial library synthesis and screening, conventional (i.e., Sanger or Maxam-Gilbert) DNA sequencing, or single-molecule DNA sequencing. In one embodiment of the invention, reaction products are left behind as the particle is moved through the thin film coating. Advantageously, these products can be identified by suitable means.

BRIEF DESCRIPTION OF THE DRAWINGS

These and other objects, features and advantages of the invention will be more readily apparent from the following detailed description of the preferred embodiment of the invention in which.

DETAILED DESCRIPTION OF PREFERRED EMBODIMENTS OF THE INVENTION

Figure 1:
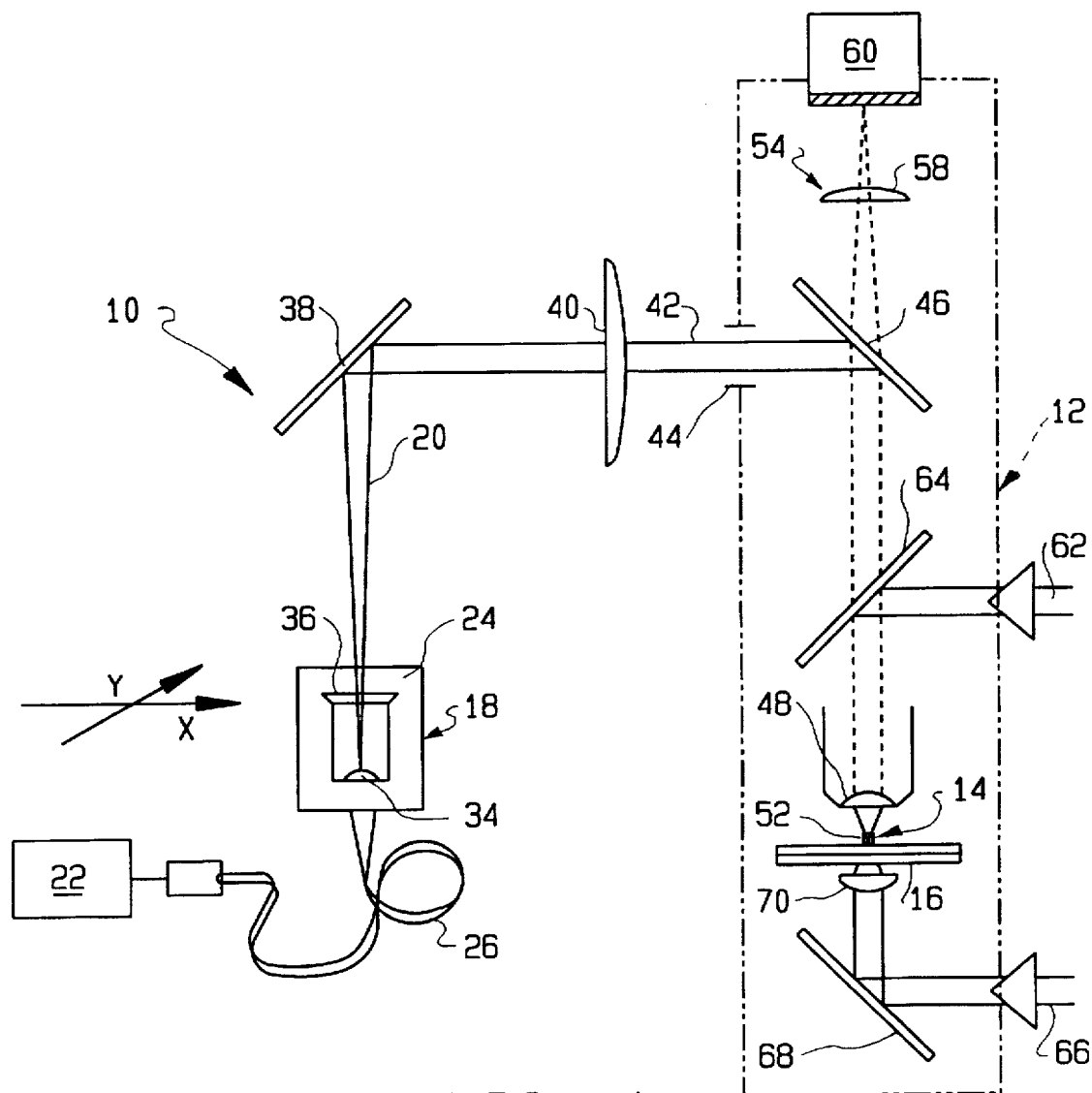
FIG. 1 is a schematic illustration of a conventional optical trap (prior art)

FIG. 1, which is reproduced from the '169 patent, depicts a conventional optical trap 10 of the type which is used in practicing the invention. The trap comprises a modified fluorescence microscope 12 including a chamber 14 containing a liquid cell where particle manipulation takes place. The chamber is mounted on a conventional microscope stage 16 which can be moved in two orthogonal directions in the plane perpendicular to the axis of the microscope, as well as along the optical axis.

The optical trap is formed by a laser beam from a laser 22 which is focused on chamber 14 by a highly convergent objective lens 48. Illustratively, the laser is an argon ion laser, a diode laser or a NdYAG laser. Lens 48 typically has a numerical aperture greater than 0.8 and preferably about 1.2 or greater. Advantageously, lens 48 is a liquid immersion type and an oil drop between lens 48 and the cover of chamber 14 approximately matches the refractive indices of the lens and the cover so as to minimize light losses at the surfaces.

The position of the optical trap in chamber 14 may be moved by moving platform 24 in the X or Y directions. Alternatively, stage 16 may be moved with respect to the optical trap.

The apparatus of FIG. 1 further comprises an image intensified video camera 60 or other electro-optical imaging device, a fluorescence light source 62 such as an argon laser or a mercury lamp and a visible light source 66.

Further details concerning this optical trap are set forth in the '169 patent. A similar such trap is illustrated in FIG. 1 of the '886 patent.

Figure 2A:
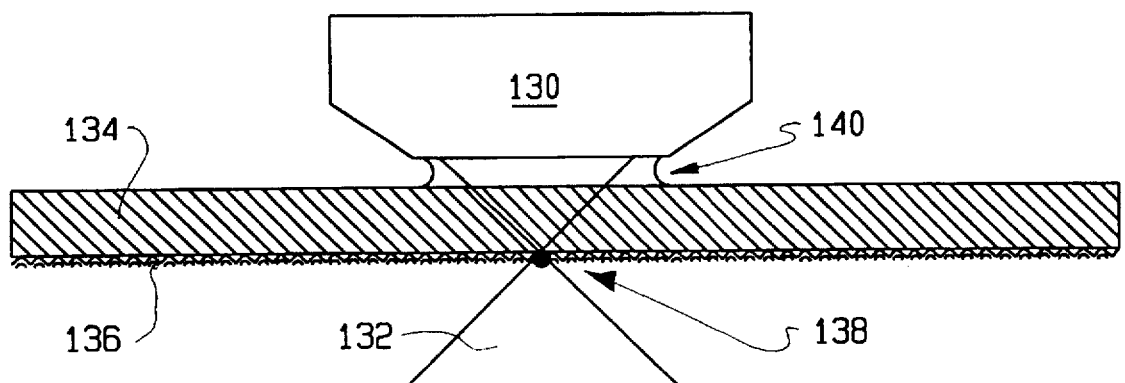
FIGS. 2A–2H are schematic illustrations of illustrative optical trap configurations used in the practice of the invention.
Figure 2B:
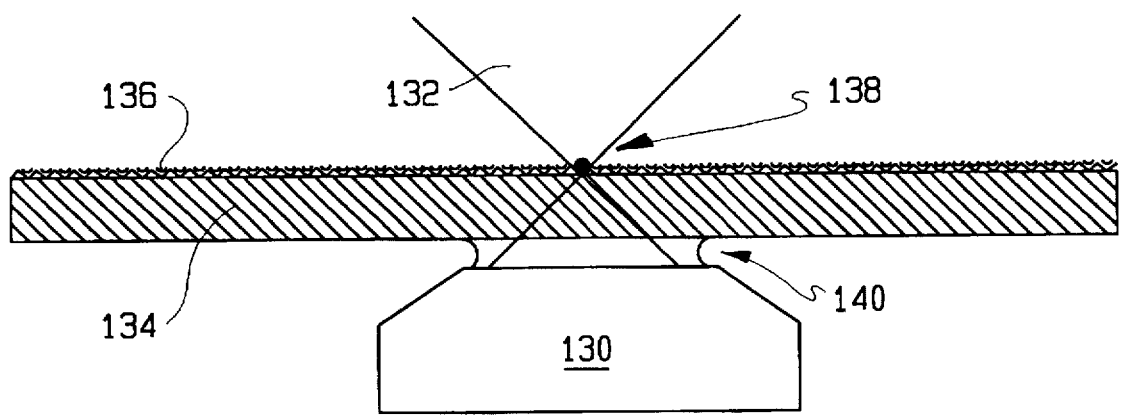

Several optical trap geometries that can be used in the practice of the invention are set forth in FIGS. 2A–2H. Each of FIGS. 2A–2E depicts an objective lens 130, an optical beam 132, a substrate 134, a thin liquid film 136 and a trapped particle 138. In FIGS. 2A and 2B, optical beam 132 is directed by objective lens 130 through substrate 134 to thin film 136 where it traps particle 138. In these figures, index-matching immersion oil 140 minimizes light losses that would otherwise be created at interfaces between the objective lens and the air and between the air and the substrate. FIG. 2A depicts the case where the thin film is coated on the underside of the substrate and FIG. 2B the case where the thin film is coated on the topside of the substrate. As will be apparent, in FIGS. 2A and 2B the substrate must be transparent to the optical beam.

Figure 2C:
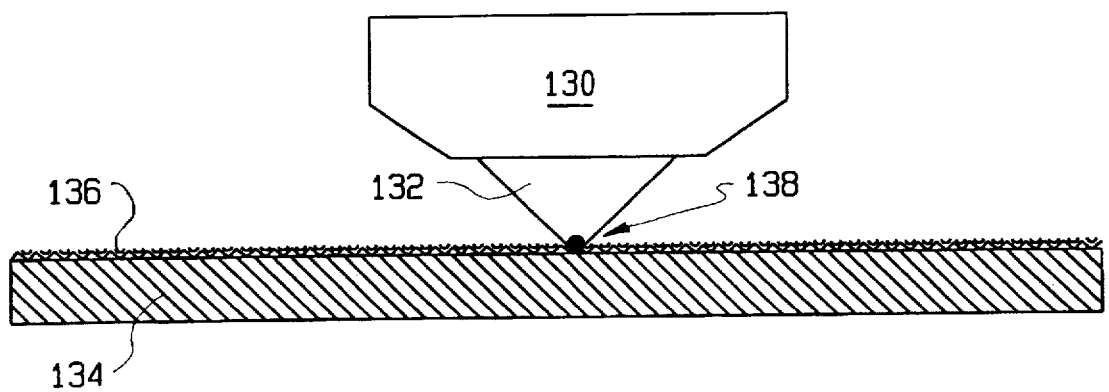
Figure 2D:
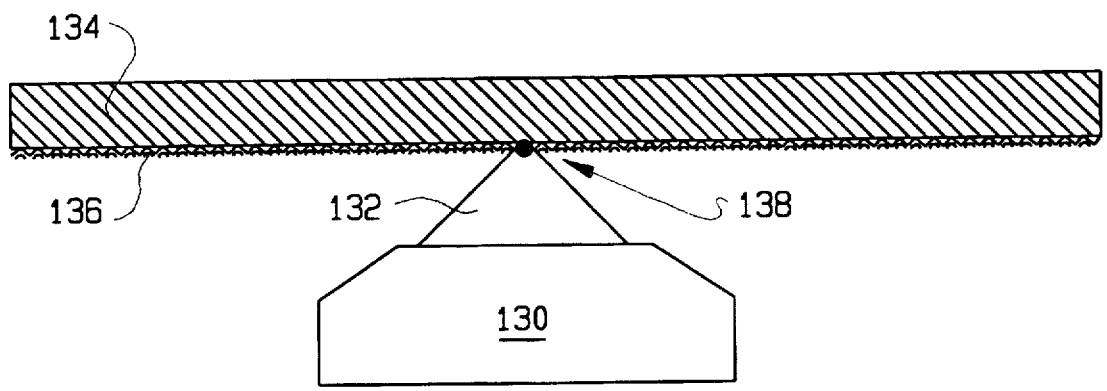

In FIGS. 2C and 2D, the optical beam is incident on the thin film from its outer surface. In this case, an immersion oil is not used and the substrate need not be transparent to the optical beam. However, to permit viewing of the thin film by a human observer using optical traps such as those of the '169 and '886 patents, the substrate should be transparent to visible light.

Figure 2E:
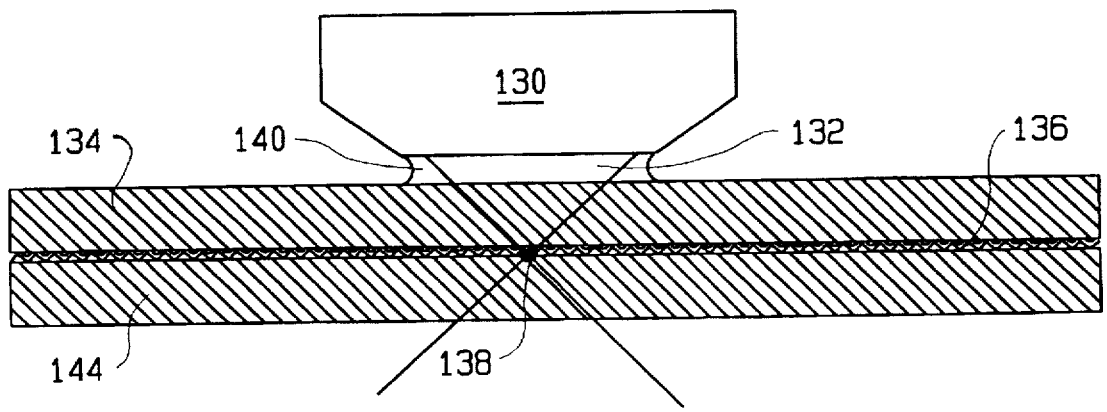

FIG. 2E is similar to FIG. 2A but depicts the case where the thin film is sandwiched between two substrates 134, 144.

Figure 2F:
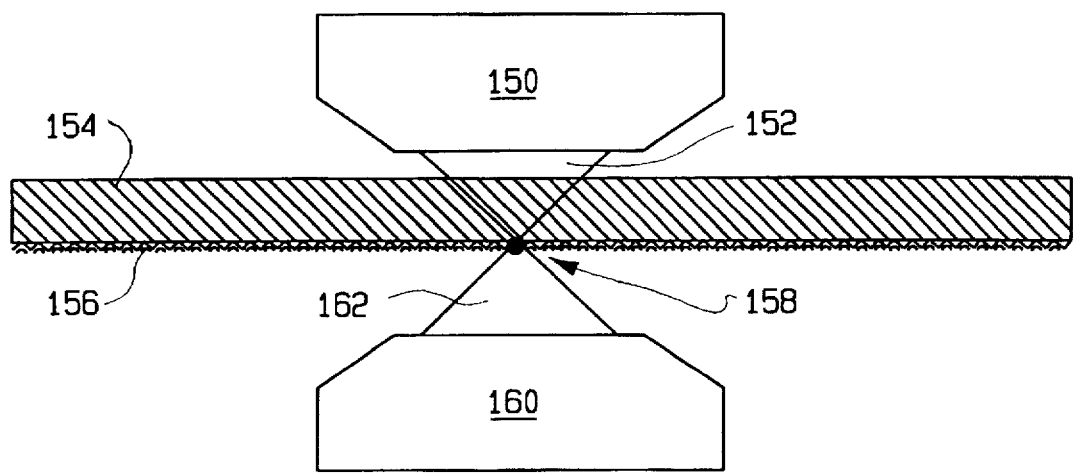
Figure 2G:
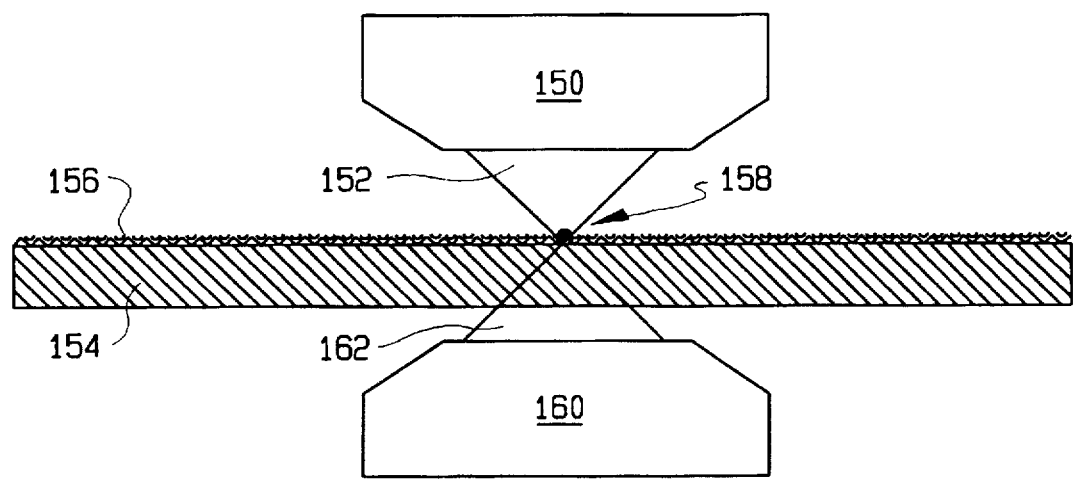
Figure 2H:
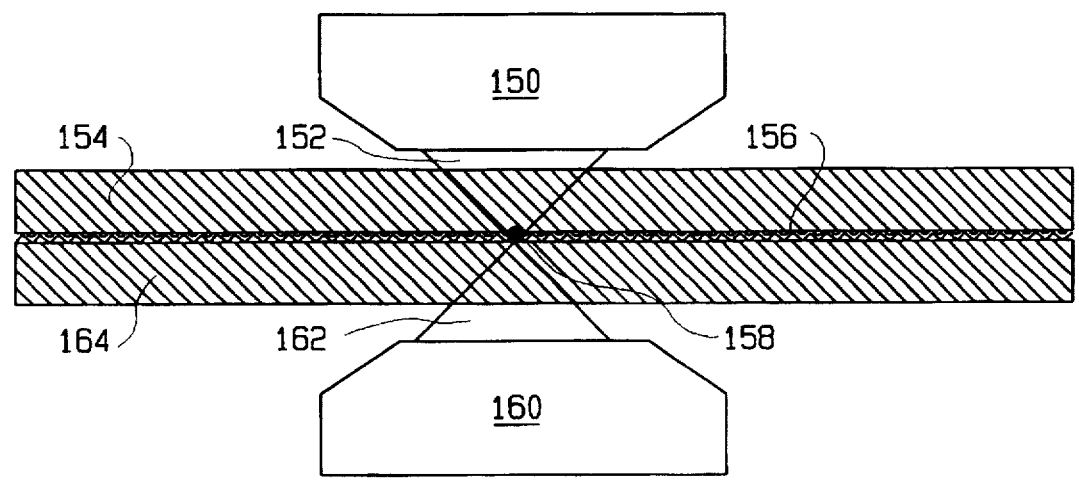

The invention may also be practiced using multiple beam optical traps. Three such geometries are shown in FIGS. 2F, 2G and 2H. Each of these figures depicts a first objecive lens 150, a first optical beam 152, a substrate 154, a thin liquid film 156, a trapped particle 158, a second objective lens 160, and a second optical beam 162. Each of these elements is similar to the corresponding elements in FIGS. 2A–2E. FIG. 2F depicts the case where the thin film is coated on the underside of the substrate and FIG. 2G, the case where the thin film is coated on the topside of the substrate. FIG. 2H depicts the case where the thin film is sandwiched between two substrates 154, 164. Optionally index-matching immersion oil objectives may be used in cases where the objective lens is on the other side of the substrate from the thin film.

Preferably the substrates are thin (e.g., 130–250 μm which is the range of typical thicknesses of standard microscope coverslips) and optically flat so as to permit the use of a high numerical aperture objective lens to form the optical trap. For cases where the objective lens is on the opposite side of the substrate from the thin film, the substrate must be highly transparent at the trapping wavelength (e.g., in the infrared at 1064 nm). For fluorescence applications the substrate should be transparent at either the wavelength of the light that excites fluorescence in the trapped particle, the wavelength of the excited fluorescence, or both. The substrate should also be free of background fluorescence either in bulk (e.g., color centers) or on the surface (i.e., fluorescent contaminants). The preferred material would be fused silica or quartz, for example in the form of a microscope coverslip or a thinned HOYA T-4040 quartz wafer (Hoya Electronics Corporation, Woodcliff Lake, N.J.).

In practicing the invention, the thin film coating can be either an aqueous or an organic liquid film, depending on the nature of the chemical, biochemical or biological reactions to be carried out in the film. Enzymatic reactions would typically be carried out in buffered aqueous films which are compatible with the enzyme, whereas organic synthesis reactions such as oligonucleotide synthesis would typically be carried out in anhydrous organic films. The thickness of the film typically is approximately the same as the diameter of the particle that is manipulated by the optical trap. The film must be thick enough to permit transport of the particle along the surface of the underlying solid substrate. The liquid film may be sandwiched between two substrates or may be coated as a surface film on a single substrate with a resulting free interface of the thin film. In this latter case, the thin film coated substrate may form one side of a "moist chamber" which is capable of controlling the relative humidity or vapor pressure of the film-forming material so as to prevent undesired evaporation of the film and to control the film thickness. The optical beam that forms the trap may be incident on the thin film from its free surface side or from the substrate side.

Several different methods may be utilized, either alone or in combinations, to create heterogeneous liquid surface films on a substrate. In one example, an optically flat substrate is coated with the thin film by any of a number of methods well-known in the art including spin coating, doctor blading or simply wetting. Droplets of the various reagents are then deposited on top of the previously applied thin film using micropipettes, either manual or automated, or various means based on ink jet printing technology which is well established in the art. The droplets typically are microscopic in size, but may be as large as 1 mm or greater, depending on the method of deposition and specific requirements for the droplet. Various agents can be included in the droplet solutions to minimize their spreading on the thin film. Such agents include viscosity-increasing agents such as glycerol or polymers, or agents which control the miscibility of the droplet in the thin film. The different droplets are deposited on the thin film with sufficient spatial and/or temporal separation so as to prevent undesired spreading and/or mixing of reagent droplets during the time frame required to complete the necessary reaction steps.

Figure 3A:
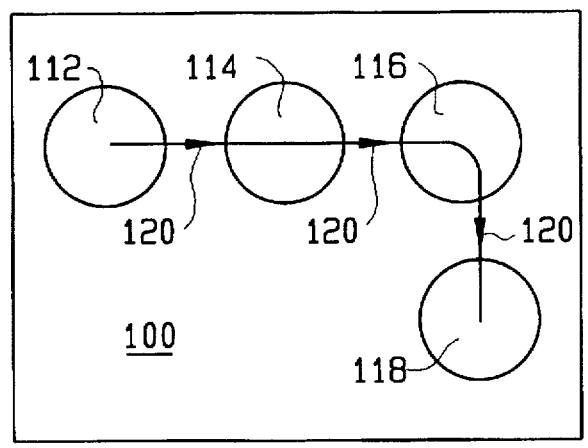
FIGS. 3A–3C are schematic illustrations of thin film coatings and reagent locations used in the practice of the invention.

In accordance with one aspect of the present invention, an optical trap such as that of FIG. 1 is used to trap a particle in one region of a heterogeneous thin liquid film coating and move the particle through a succession of different regions of the thin film coating where different chemical, biochemical and/or biological processes take place. For example, with reference to FIG. 3A which is a top view of a thin liquid film coating 100, a series of droplets 112, 114, 116, 118 may be deposited in thin film coating 100. Each droplet contains a different chemical or biochemical or a different biological agent. Using the optical trap, a particle may be selected in droplet 112 and then moved successively through thin film coating 100 to droplet 114, droplet 116 and droplet 118 as indicated by arrows 120. In each successive droplet some chemical, biochemical or biological process takes place so as to produce in droplet 118 the product that is desired.

Figure 3B:
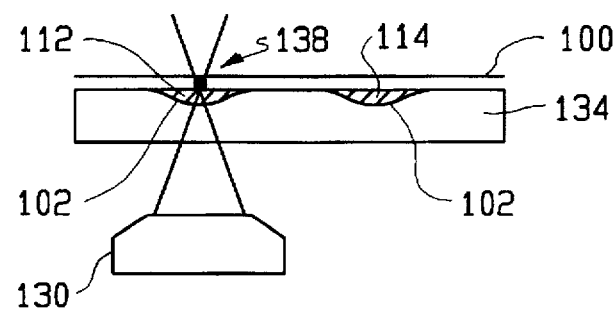
Figure 3C:
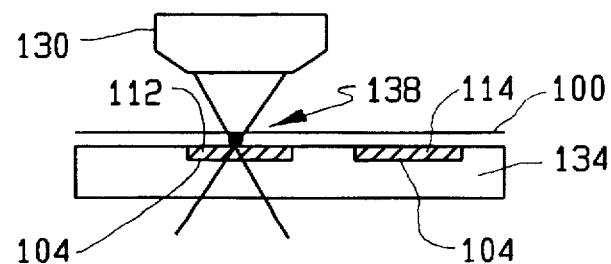

Various features such as wells 102, 104 may be formed in the solid substrate to facilitate the placement and separation of reagent droplets as illustrated in the side views of FIGS. 3B and 3C. Such features can be formed in the substrate by various means including lithography and etching, stamping or molding, or micromachining. Such a pre-formed substrate may be coated with the thin film as described above, and then the various sample wells, micro channels or microchambers loaded with their proper reagents through the thin film coating, or the reagent chambers may be loaded first and then the thin film coating applied. The reagents may include various agents to increase their density above that of the thin film so that the reagent will settle into the depression in the substrate and displace the film. This is similar to the manner in which the well of an electrophoresis gel is typically loaded. Indicator dyes are often added to such reagents in order to more easily visualize the loading process. Such dyes, if used, must obviously be compatible with the reagent and any processing step which is to occur in that reagent location. A particle can be moved vertically with the optical trap to introduce it to the reagent pool and then vertically withdrawn for horizontal transport to adjacent reagent locations via the thin film. If optical trapping is to be performed through a substrate containing pre-formed features (i.e., not optically flat) such as wells 102 of FIG. 3B or 104 of FIG. 3C, those features must be designed and fashioned in such a manner that they do not interfere with the trapping beam. For example, abrupt vertical changes in surface features are to be avoided. If optical trapping is to be performed from the thin film side, such constraints are less important as depicted in FIG. 3C.

Another method for effectively creating heterogeneous thin liquid films and/or heterogeneous substrate surface chemistries would include molecular self-assembly and nanochemistry (1992), Abbott et al., Science 257:1380; (1991), Whitesides et al., Science 254:1312, which are incorporated herein by reference). Such methods can extend the range of combinations of reagents utilized.

The present invention is useful in many routine chemical, biological and biochemical procedures and provides a simple means for scaling reactions to submicroliter levels without the difficulty and complexity of plumbing systems capable of operating at this level.

For example, oligonucleotide synthesis is used to synthesize short, single-stranded DNA molecules for use as hybridization probes and DNA sequencing primers. Current methods often produce a vast excess of product due to the limitations on the scale of synthesis. Applications such as directed DNA sequencing are currently limited by the cost of such syntheses. In the present invention, oligonucleotide synthesis can be carried out on a single particle of commercially available beads which are coupled to the first nucleotide of a desired sequence. Coupling of successive nucleotides using standard phosphoramidite chemistry can easily be carried out in this thin film format.

In particular, a series of droplets are deposited on a thin film, one droplet containing the beads to which are attached a first reactive nucleotide of the desired sequence and the other droplets each containing numerous molecules of the same reactive nucleotide with a different nucleotide in each droplet. Coupling reagents deblocking reagents, capping reagents or washing reagents could be located in different droplets. A single bead is then selected by the optical trap from the droplet containing the beads. By moving the optical trap relative to the thin film, the trapped bead is then moved through the thin film to a droplet containing nucleotides of the type that is next to be coupled to the nucleotide already attached to the bead. This process is repeated additional times always moving the trapped bead and attached nucleotides to the next droplet in the order in which it is desired to assemble the sequence of nucleotides.

Upon completion of the synthesis, the oligonucleotide can be cleaved from its bead and coupled directly into a thin film version of the solid-phase format of the Sanger DNA sequencing method which is also performed on the surface of a bead. The final sequencing reaction products could then be released into the sample chamber of a capillary electrophoresis system which has been microfabricated into the same substrate. Such a method could also be applied to the sequencing of oligonucleotide tags from encoded combinatorial libraries (Brenner & Lerner, Proc. Natl. Acad. Sci. USA 89:5381–5383 (1992), which is incorporated herein by reference.

Similarly, the Edmann sequencing chemistry for peptides can be adapted to the thin film format for directly sequencing from single beads. Such methods would be particularly important for further reducing the mass of naturally-occurring proteins required for sequencing, and also for sequencing peptide tags from combinatorial libraries (Lam et al., Nature 354:82–84 (1991); Lam et al., Bioorganic & Medicinal Chemistry Letters 3(3):419–424 (1993), which are incorporated herein by reference.

Synthesis of peptides (Furka et al., Intl. J. Peptide Protein Res. 37:487–493 (1991)), peptoids (Simon et al., Proc. Natl. Acad. Sci. USA 89:9367–9371 (1992), Bartlett et al. WO 91/19735), macromolecules (Schrober et al., BioTechniques 18(4);652–660 (1995)) and other combinatorial libraries (e.g., Ellman, U.S. Pat. No. 5,288,514; Bunin and Ellman, J. Am. Chem. Soc. 114:10997–10998 (1992)), all of which are incorporated herein by reference, can also be adapted to the thin film format of the present invention. Essentially any chemical or biochemical synthesis or sequencing reaction which can be carried out on a solid-phase support, typically a bead, can be scaled to operate at the level of single beads using the present invention.

In those instances where reaction products must be monitored or, for example, binding constants measured, the fluorescence correlation spectroscopy methods of Rigler can be applied to analyzing the contents of submicroliter samples in the thin film (Eigen and Rigler, (1994) Proc. Natl. Acad. Sci. USA 91:5740–5747, which is incorporated herein by reference).

The present invention is also useful in biological procedures where the procedure includes a step involving the isolation of a desired substance from among a large number of undesired substances. By way of illustration, examples of such biological procedures are: production of monoclonal antibodies, screening of phage display peptide libraries, and cloning of nucleic acids.

For production of monoclonal antibodies, the present invention can be readily adapted for use in selecting a single cell that produces a desired monoclonal antibody from a background of a large number of cells that produce undesired, or no, monoclonal antibodies. The generation of monoclonal antibodies involves the selection of an antigen for which it is desired to have monoclonal antibodies that are capable of specifically binding that antigen. Such an antigen might be a protein, nucleic acid, polysaccharide, or any other material for which it is desired to have monoclonal antibodies that specifically bind that material. In a particular embodiment of the present invention, the antigen is coupled to a particle that is suitable for trapping in the optical trap. Such a particle might be a latex bead, for example.

In applying the invention to the production of monoclonal antibodies, the first droplet 112 contains one or more of the appropriate particle-coupled antigens. One of these particle-coupled antigens is then trapped in the optical beam of the optical trap and is moved through thin film 110 to second droplet 114. The second droplet 114 contains a variety of monoclonal antibody producing cells, some of which produce monoclonal antibodies that are specific to the antigen. Such monoclonal antibodies may be produced by standard methods well known in the art. See, e.g. Kohler and Milstein, Nature 256:495–497 (1975); Kozbor et al., Immunology Today 4:72 (1983); Cole et al., Monoclonal Antibodies and Cancer Therapy, pp. 77–96 (Alan R. Liss, Inc., 1985).

Conditions are chosen in the second droplet 114 so that the particle-coupled antigen binds to a monoclonal antibody-producing cell that contains monoclonal antibodies that are specific for the antigen coupled to the particle. The optical trap is then used to move the particle-coupled antigen together with the bound monoclonal antibody-producing cell through thin film 110 into the next droplet 116, thus separating the desired monoclonal antibody-producing cell from the background of undesired cells. The desired monoclonal antibody-producing cell is then collected from droplet 116 and placed in appropriate culture conditions to permit replication of the cell into a cell line that produces the desired monoclonal antibodies.

In a similar manner, the present invention may be used to screen a phage display peptide library in order to select a phage that displays a desired peptide from a vast background of phage expressing undesired peptides. A ligand for which it is desired to have a peptide that binds to the ligand is coupled to a particle. One or more of the particle-coupled ligands are applied to thin film 110 in the form of first droplet 112. The optical trap is used to trap a single particle-coupled ligand in its optical beam and move it through thin film 110 to second droplet 114. The second droplet 114 contains an aliquot of a phage display peptide library. The library can be made by any of a variety of well known techniques. See e.g. Smith, Science 228: 1315–1317 (1985); De la Cruz et al., J. Biol. Chem. 263: 4318–4322 (1988); Parmley and Smith, Gene 73: 305–318 (1988); Parmley and Smith, Adv. Exp. Med. Biol. 251:215–218 (1989); Scott and Smith, Science 249:386–390 (1990).

If the aliquot of the phage display peptide library contains a phage that displays a peptide capable of specifically binding to the ligand, that phage will bind to the particle-coupled ligand and be carried along with the particle coupled ligand. The optical trap is then used to move the particle-coupled ligand through thin film 110 to the next droplet 116. From droplet 116 the desired phage can be recovered and grown in suitable bacterial hosts for analysis and/or purification of the desired peptide.

The present invention may also be used to purify desired nucleic acid fragments from a collection of nucleic acid fragments such as a genomic or cDNA library. For example, when making a genomic library, present techniques often involve the steps of isolating an organism's total DNA and then cleaving that DNA with a suitable restriction enzyme. This is followed by procedures which permit the identification and isolation of the desired DNA fragment from among the background of undesired DNA fragments. The optical trap described herein may be used to simplify or obviate these latter procedures.

As for the conventional procedures, a probe (a nucleic acid fragment that specifically binds to the desired nucleic acid fragment) is necessary. The probe is coupled to a particle suitable for trapping in the optical trap. One or more of the particle-coupled probes are then applied to thin film 110 in a first droplet 112. The optical trap is then used to select one of the particle-coupled probes in its optical beam and move the particle-coupled probe through thin film 110 into the second droplet 114. The second droplet 114 contains a restriction enzyme digest of an organism's DNA. Conditions in the second droplet 114 are chosen so that if the probe is capable of specifically binding any of the fragments of the organism's DNA, it will do so, thus forming a complex of particle-coupled probe and desired DNA fragment. This complex is then moved by the optical trap through thin film 110 to another droplet 116 where it can be collected and manipulated as desired.

A preferred application of the invention is to base-at-a-time single molecule DNA sequencing. In this application the particle is a single strand of DNA attached at one end to a microscopic bead. A single such bead and attached DNA strand is selected by use of an optical trap from a droplet in the thin film coating containing a large number of such beads and attached strands. By moving the optical trap relative to the thin film coating, a selected bead is then moved through the thin film coating to a droplet containing processive exonucleases where a single exonuclease binds itself to the free end of the DNA strand. The optical trap then translates the bead, DNA strand and exonuclease to a portion of the thin film coating where the exonuclease is activated. As a result, the exonuclease begins to cleave single nucleotides one-at-a-time from the DNA strand. The optical trap then draws the bead, strand and exonuclease through the thin film while the exonuclease cleaves single nucleotides from the DNA strand, leaving them behind in the path defined by the movement of the DNA strand.

A suitable detection system then re-traces the path of the DNA detecting and identifying the nucleotides in proper sequence. An illustrative such system is a pulsed laser which repeatedly stimulates fluorescence from the single nucleotides and an optical detection system which detects the different time-resolved fluorescence spectra associated with the different nucleotides.

This application is illustrated in greater detail in FIGS. 4A–4E.

For those single nucleotide identification schemes which either excite the fluorescence of the single nucleotides and/or detect single nucleotide emissions through the substrate, the substrate must be transparent in the UV (240–300 nm) and/or near UV (300–450 nm) for native nucleotide excitation and detection respectively. For variations of the method which employ one or more fluorescent nucleotide analogs and/or dye-tagged nucleotides, the substrate must be highly transparent in the corresponding excitation and emission wavelength regions.

In order to translate a DNA molecule across the substrate surface, it is necessary to provide a minimal-thickness aqueous film on the surface of the substrate. Since the bead attached to the DNA can be 0.2–1.0 µm in diameter, a film of comparable thickness should be adequate. The liquid film can be as simple as a purely aqueous buffer appropriate for the exonuclease, or might include various agents which are compatible with the exonuclease to increase the viscosity of the film (e.g., glycerol). The film might also include polymers or pre-polymers, either free in solution or covalently attached to the substrate (Hjertén, J. Chromatography 347:191–198 (1985) which is incorporated herein by reference). The increased viscosity of such films will reduce the diffusion of the released single nucleotides (Pratt and Keller, J. Phys. Chem. 97:10254–10255 (1993), which is incorporated herein by reference). In order to prevent evaporation of the surface film during single nucleotide presentation, the film can be sandwiched between two substrates as in FIGS. 3E or 3H with the appropriate separation. This would preclude the use of near field optics for single nucleotide detection, but would be compatible with far field optics. Alternatively, the thin film may have a free surface where the relative humidity of the gas phase in contact with the film is controlled so as to prevent evaporation or condensation. Such films with free surfaces may be applied to the substrate by means well known in the art, such as spin coating (Betzig and Chichester, Science 262:1422–1425 (1993) which is incorporated herein by reference).

Single, large DNA molecules are coupled to beads by various methods previously described in my co-pending U.S. Pat. application Ser. No. 08/376,761; Perkins et al., Science 264:819–822 (1994a), Science 264:822–825 (1994b), Science 268:83–87 (1995), which are incorporated herein by reference or otherwise known in the art.

Figure 4A:
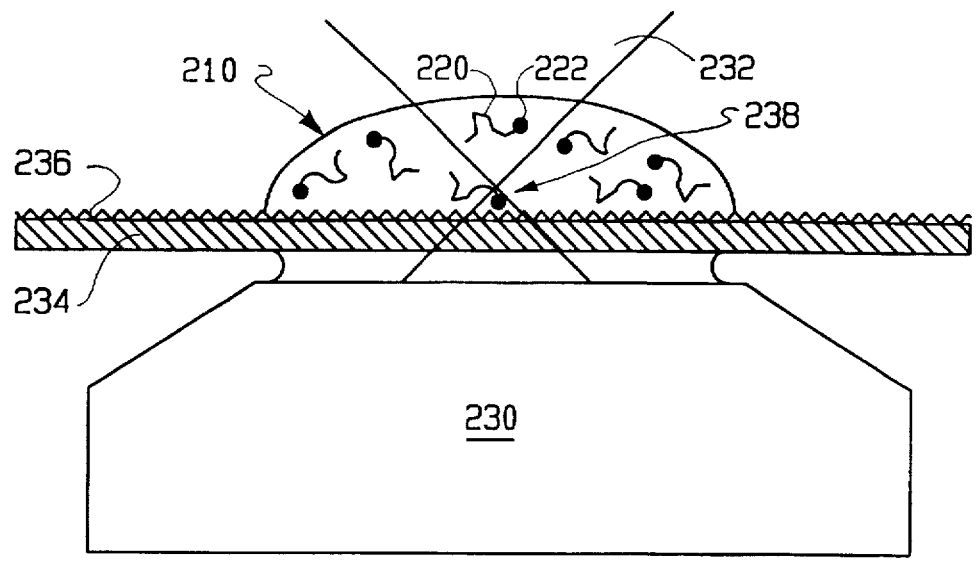
FIGS. 4A–4E are schematic illustrations of a preferred embodiment of the invention.
Figure 4B:
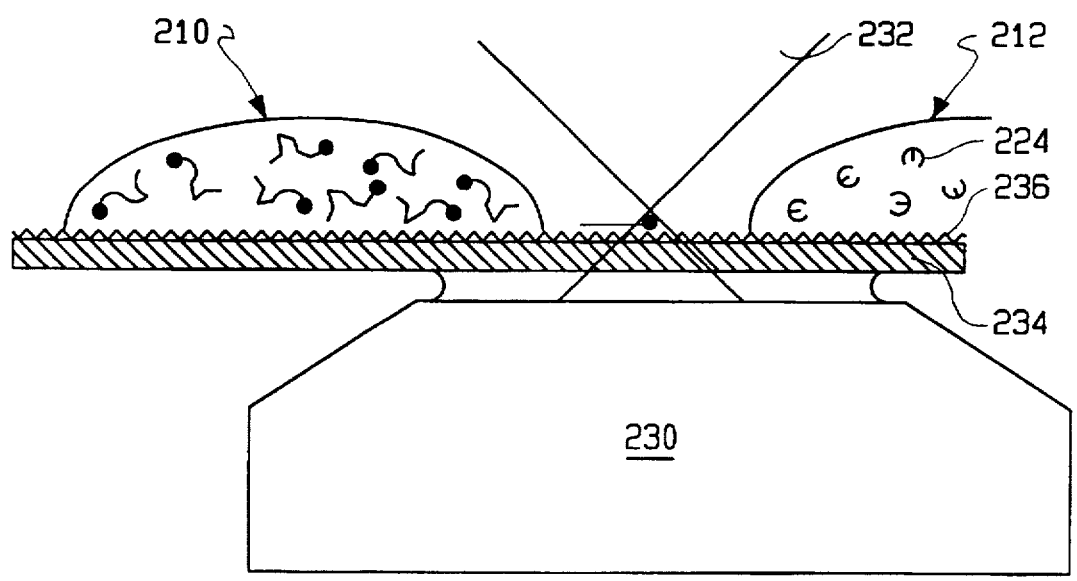

The simplest means for introducing a sample of DNA attached to beads is to use an inverted microscope configuration with the objective lens for the optical trap below the transparent substrate and the thin film on the upper surface of the substrate as shown in FIG. 2B. As shown in FIG. 4A, a microliter or sub-microliter droplet 210 containing DNA 220 coupled to beads 222 is deposited on a thin film 236 on a substrate 234. A single bead+DNA molecule 238 is selected visually for trapping in an optical beam 232 from objective lens 230. As shown in FIG. 4B, the single bead +DNA molecule is then translated out of the droplet and through the thin film as a result of relative movement of the substrate and the objective lens. Other unselected beads and DNA remain located at the position of the droplet. Similar methods can be adapted for the other geometries of FIGS. 3A–3H.

Figure 4C:
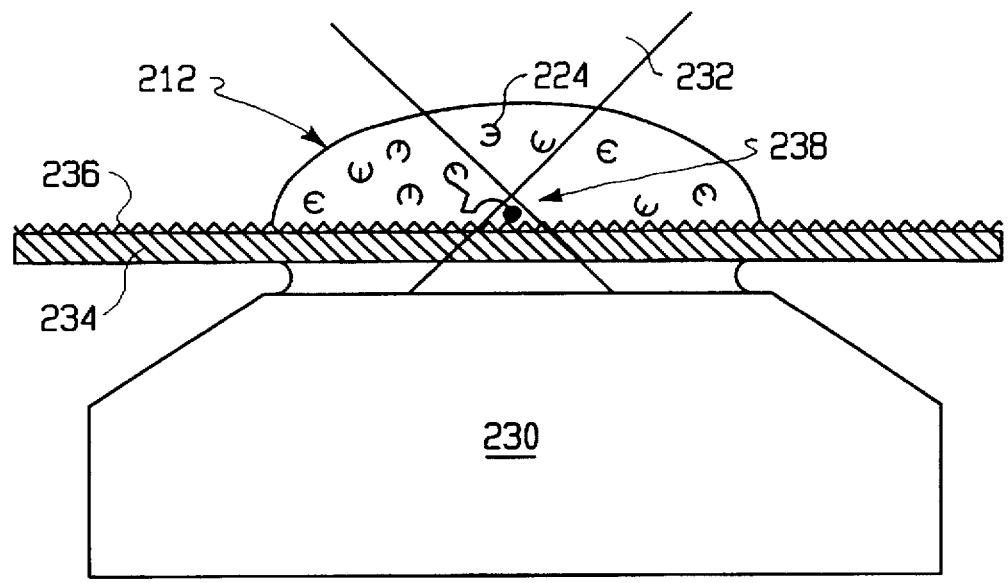
Figure 4D:
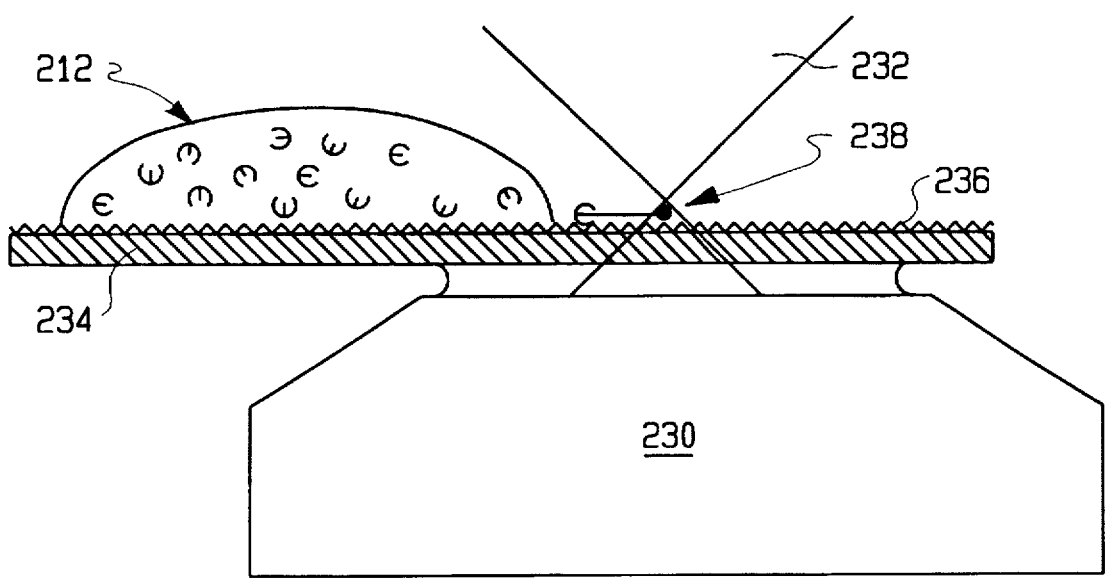
Figure 4E:
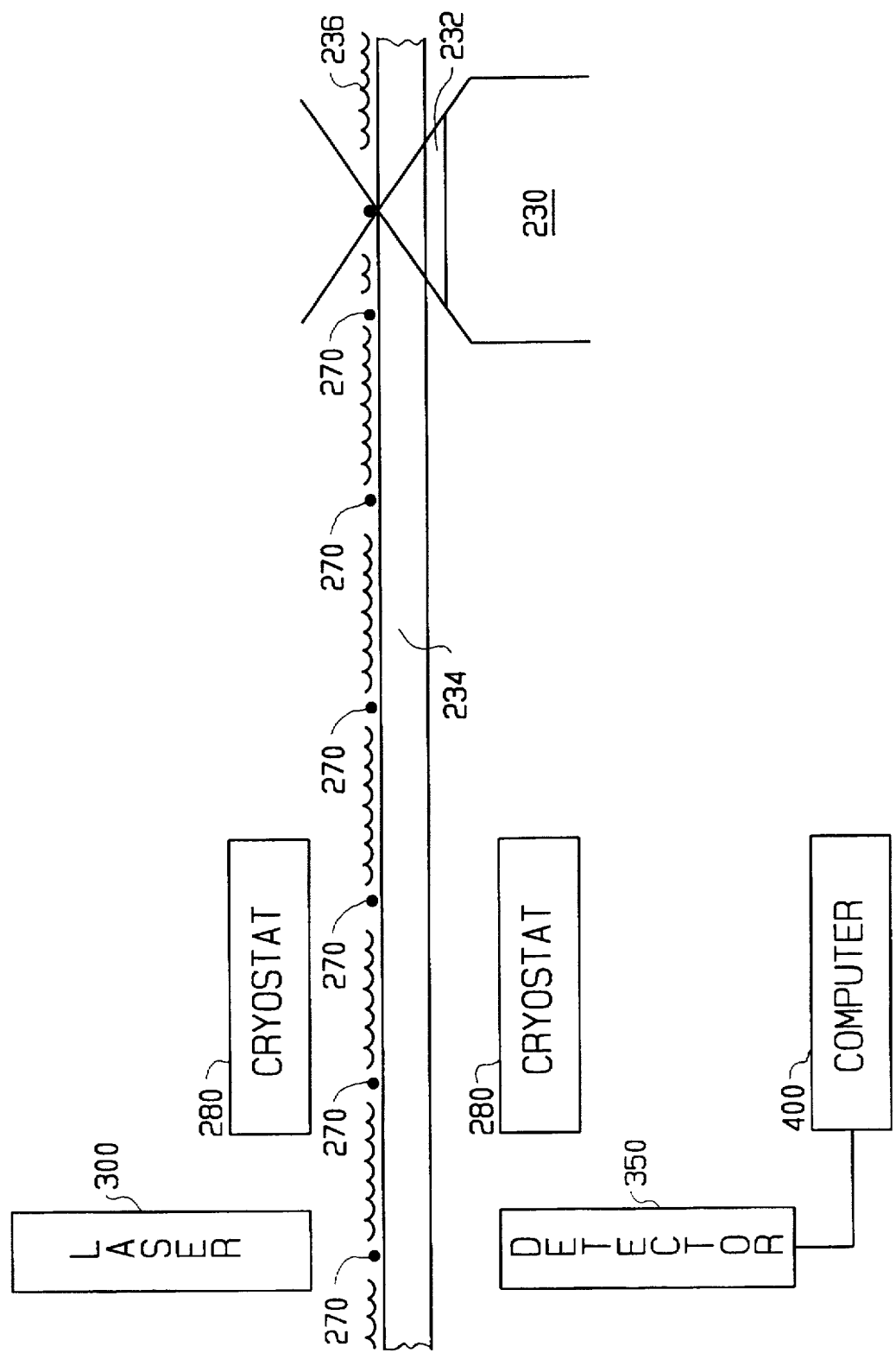

As shown in FIG. 4B, a second microliter or submicroliter droplet 212 containing an appropriate concentration of exonuclease 224 is placed on thin film 236 immediately adjacent to the droplet 210 containing beads and DNA. As shown in FIG. 4C, the single selected bead+DNA complex is translated through this second droplet to allow binding of a single processive exonuclease molecule 224 to the free end of the DNA. As shown in FIG. 4D, the bead+DNA+exonuclease complex is then translated out of the second droplet 212 and through the thin film across the surface where exonucleolytic cleavage takes place. As shown in FIG. 4E, this results in a sequence of nucleotides 270 being left behind in thin film 236 as the bead-DNA-exonuclease complex is moved through the film.

The single bead+DNA+exonuclease complex can be translated through the thin film across the substrate surface in any pattern which does not scramble the trail of single cleaved nucleotides. For example, the path may define a concentric spiral on the surface of a disk-shaped substrate, similar to the groove pattern of a phonograph record or a back-and-forth pattern similar to a raster scan as illustrated in FIG. 13 of my '761 application. Most simply, the complex can be translated unidirectionally through the thin film to define a simple, linear path. For those thin films containing polymers, the single DNA complex will reptate through the polymer matrix (i.e., the exonuclease-bound end of the DNA molecule will strictly follow the path defined by the movement of the bead-bound end of the DNA) Perkins et al., 1994a, supra.

It is desirable to minimize the two-dimensional diffusion of individual cleaved nucleotides across the surface so as to permit the closest possible spacing of cleaved nucleotides without scrambling their proper sequential order (Pratt and Keller, supra). A variety of means can be employed to minimize diffusion. One of the simplest is to increase the viscosity of the liquid surface film as outlined above and control the spacing of released single nucleotides by appropriately regulating the turnover number of the exonuclease (e.g., by varying the temperature) and the rate of translation of the single DNA molecule through the thin film. In addition, it is possible to cross-link a polymer film on the surface in the trail behind the DNA containing the single nucleotides by following the path with a second focused laser beam which photo-crosslinks the polymer but does not photobleach the released single nucleotides. With the right selection of polymer, it is possible to photo-crosslink with the infrared trapping beam if the cross-linking time is adjusted to be long enough to allow the extended DNA chain to pass first. It is also possible to modify the surface chemistry of the substrate so as to provide very high binding capacity for nucleotide monophosphates, for example, through electrostatic interactions with the negatively charged phosphate group (Matheja and Degens, "Structural Molecular Biology of Phosphates", Fortschritte Der Evolutionsforschung, Band V, Gustav Fischer Verlag, Stuttgart, 1971. pp. 180, which is incorporated herein by reference). Anion exchange reagents typically used to bind nucleotide monophosphates may be employed. Alternatively, proteins or organic and inorganic complexing agents (Kyogoku, Lord and Rich, Proc. Natl. Acad. Sci. USA, 57:250–257 (1967); Kyogoku, Lord and Rich, Nature 218:69–72 (1968); Kim and Rich, Proc. Natl. Acad. Sci. USA, 60:402–408 (1968); Terron and Moreno, Inorganica Chimica Acta 56:L57–L59 (1981), which are incorporated herein by reference) which specifically bind to the different nucleotide monophosphates can be bound to the substrate surface, serving as effective traps for the released mononulceotides. Self-assembled monolayers on the substrate can be utilized to provide such nucleotide binding capacity. The oriented nature of such self-assembled monolayers will also serve to orient the bound nucleotides to facilitate detection.

The diffusion of released single nucleotides is further reduced by cooling the substrate to cryogenic temperatures (about 77° K) so as to form a rigid, hydrophilic glass matrix from the thin film which entraps the isolated individual nucleotides. Further details are found in my co-pending '761 application. The low temperature and the highly cohesive matrix further serve to greatly enhance the photostability and quantum yield of fluorescence of the nucleotides to facilitate their subsequent detection and identification. Apparatus for cooling the thin film substrate includes designs similar to that of Grober et al., Rev. Sci. Instrum. 65(3):626–631 (1994), which is incorporated herein by reference) or commercially-available instruments such as the model CF2102 Microscope Cryostat (Oxford Instruments, Concord, Mass.). In FIG. 4E the substrate is cooled to cryogenic temperatures by cryostat 280.

If the individual cleaved nucleotides are separated sufficiently, they are detectable on the surface using conventional, diffraction-limited optics as described in detail in my co-pending '761 application and more recently in Tellinghuisen et al., Anal. Chem. 66(1):64–72 (1994) and Nie et al., Science 266:1018–1021 (1994), which are incorporated herein by reference. If the nucleotides can be immobilized so as to prevent scrambling of their proper sequential order at even closer spacing, then near field scanning optical microscopy can be employed. In the latter case, however, the nucleotides must be localized on the surface of the thin film so that the scanning probe tip can approach within about 3 times the diameter of the probe opening. This may reqyre evaporation or sublimation of some or all of the thin film, prior to nucleotide detection, and in a manner which does not cause loss of the nucleotides from the substrate surface. At greater distances, far field optical conditions apply. Recent examples of single-molecule fluorescence spectroscopy on surfaces using near-field optics include Betzig and Chichester, supra; Ambrose et al., Phys. Rev. Lett. 72(1):160–163 (1994a); Trautman et al., Nature 369:40–42 (1994); Xie and Dunn, Science 265:361–364 (1994); and Ambrose et al., Science 265:364–367 (1994b), which are incorporated herein by reference.

In FIG. 4E, a fluorescence spectroscopy system is depicted including a laser system 300, a detector 350 and a computer 400. Further details of this system are set forth in FIG. 5 which has been adopted from FIG. 9 of my '761 application. Briefly, the system is a time-resolved single photon counting system in which a laser beam 305 repeatedly excites each nucleotide 270 into fluorescence and detector 350 measures the delay in arrival time of the single fluorescent photon after each laser pulse. By doing this numerous times for each nucleotide to be detected, it is possible to accumulate a large statistical sample of single fluorescent photon events from which the fluorescent half-life of each nucleotide can be determined. This measurement of half-life can then be compared by computer 400 with previously measured half-lives of known nucleotides to locate the best match and thereby identify the nucleotide.

Laser beam 305 is generated by a coherent radiation source which preferably is a mode-locked laser 310. In a preferred embodiment, laser 310 comprises an argon ion pumped, mode-locked Ti:sapphire laser whose output is frequency tripled to provide tunable femto- or picosecond pulses over the wavelength range of 240–300 nm at a mode-locked rate of 81.5 MHz. Suitable argon and mode-locked Ti:sapphire lasers are available as Models 2080-15 and 3960 respectively from Spectra-Physics. Devices suitable for generating second and third harmonic output from the Ti:sapphire laser are the Model 5-050 frequency tripler available from INRAD in Northvale, N.J.

In alternative embodiments of the present invention in which fluorescent nucleotide analogs, dye-tagged nucleotides or various combinations of native nucleotides, fluorescent nucleotide analogs, and/or dye-tagged nucleotides are incorporated into the DNA to be sequenced, it will be obvious to one skilled in the art that the laser excitation source will need to be modified from that described supra so as to provide optimal excitation wavelengths for the types of nucleotides employed. Fluorescent nucleotide analogs and dye-tagged nucleotides typically have excitation maxima in the near UV or visible range, unlike native nucleotides. In general, such wavelengths are easier to generate with available laser technology than the deeper UV. In the most complex situation, four discrete laser sources may be required to provide optimal excitation for four different types of nucleotides.

The full time-resolved emission spectrum of each individual nucleotide is recorded by employing a streak camera in detector 350. This arrangement provides a measurement of the 3-D contour of the fluorescence intensity versus time and wavelength. At the time nucleotide 270 is irradiated by laser beam 305, a signal 337 is generated indicating the onset of a laser pulse. Illustratively, signal 337 is generated by inserting a beam-splitter 315 into the path of laser beam 305 so as to split off an auxiliary laser beam 307. Beam 307 is incident on a fast photodiode 320 which produces an output signal that is supplied to discriminator 322. Discriminator 322 is set to generate an output signal 337 representing the occurrence of an excitation pulse from laser 310 only when the number of photoelectrons incident on photodiode 320 exceeds a threshold value, thereby eliminating false detection.

Fluorescence emission 330 from the nucleotide is collected by a high numerical aperture lens 345, spatially and spectrally filtered, directed through a grating spectragraph 370, or other dispersive element such as a prism or a monochromator, and focused onto a photocathode 375. Prism 370 disperses incident photons, deviating the path of the photons along the x-axis according to their wavelength. Wavelengths outside of the fluorescent emission band of the nucleotides are excluded by such means.

Figure 5:
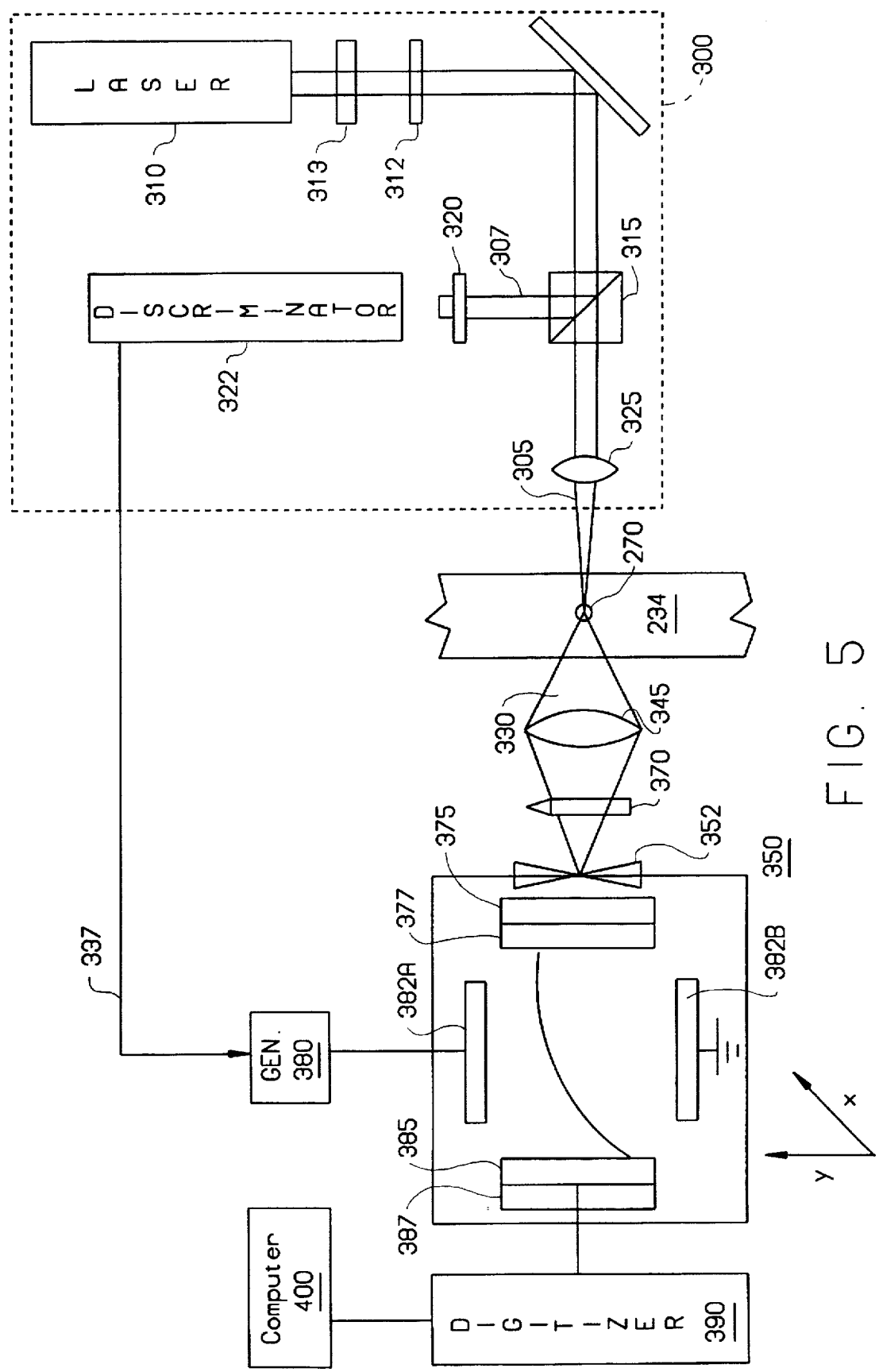
FIG. 5 is a schematic illustration of a preferred fluorescence system used in the practice of the invention.

Signal 337 is used to synchronize the mode-locked frequency of the laser with a sinusoidal voltage generator 380 to trigger high voltage sweeps across orthogonal electrode pairs, one pair of which is shown as electrodes 382A and B in FIG. 5 and the other pair of which is at right angles thereto. Advantageously, the sweep frequency is such that only a single sweep takes place between successive laser pulses. The single photo-electron emitted when the single fluorescent photon strikes photo-cathode 375 is accelerated in the high vacuum inside the streak tube by extraction grid 377 and experiences a unique electrical field that is a function of the time of emission of the single photon after the laser pulse. As a result, the single photo-electron strikes microchannel plate 385 at a point along the y-axis proportional to its emission time. Accordingly, the spatial coordinates of the photoelectron incident on micro-channel plate 385 are representative of the delay time and wavelength of each detected photon. These coordinates are digitized by digitizer 390 and provided to computer 400.

As long as the nucleotide remains within the excitation region, the nucleotide goes through repeated cycles of excitation and emission. For each fluorescent photon that is detected, the time of detection is converted to a spatial coordinate along the y-axis and the wavelength is converted to a spatial coordinate along the x-axis. These spatial coordinates are digitized by digitizer 390 and provided to computer 400. As a result, for a large number of detections, a histogram is developed which records the number of photons detected in appropriate time intervals after irradiation and appropriate wavelengths. For each of the four nucleotides, these histograms are characteristic.

Accordingly, to identify each nucleotide, the histogram that is generated for each detected nucleotide is compared with the previously recorded reference histograms of each of the four nucleotides. To this end, the previously recorded reference histograms are stored in computer 400; and as each histogram of a detected nucleotide is generated, it is compared by computer 400 with the stored histograms.

Illustratively, spectragraph 370 is a Chromex 250i-FX and the streak camera is a Model C1587 supplied by Hamamatsu Photonics of Bridgewater, N.J. The digitizer is a CCD camera and the computer is a Macintosh Quadra 840 A/V.

Further details of the apparatus of FIG. 5 are set forth in the discussion of FIG. 9 in the '761 application which is incorporated herein by reference.

As will be apparent from the foregoing, my invention may be practiced in numerous ways. Different types of optical traps can be used, different means can be employed to generate relative movement between the optical trap and the substrate and a variety of different movement patterns can be followed. It makes no difference whether the substrate is moved and the trap remains motionless or the trap is moved and the substrate remains motionless. While the invention has been described in the context of a single optical trap, greater throughput can be achieved with a multi-position optical trap.

A multiposition-scanning laser trap (Misawa et al., Macromolecules 26:282–286 (1993), which is incorporated herein by reference) can be used to translate multiple single-molecule complexes in parallel for increased sample throughput. Such a trap is formed by computer-controlled scanning of a single focused laser beam throughout the object plane with a certain speed and pattern. Several particles can be trapped simultaneously if the time between successive scans is sufficiently short. If each successive scanning pattern is slightly different, the particles can be moved independently. Commercial versions of such multi-position optical traps are available (e.g., Multi Beam Photonic Tweezers III, S+L Heidelberg, Heidelberg, Germany). Adjacent extended DNA molecules in such a multitrap configuration must be separated sufficiently so as to prevent the diffusional scrambling of the released nucleotides from either strand.

Other means may be used to transport particles from one droplet to another through the thin film. For example, by using magnetic particles or particles having a core made of a material such as iron which is attracted to a magnet, it is possible to move the particle through the thin film using magnetic fields instead of an optical trap.

In the embodiment of the invention described in conjunction with FIGS. 4A–4E, operating parameters are provided which allow for the accurate detection and discrimination of each of the native nucleotides. It will be recognized that there are many alternative embodiments where, for various reasons (e.g., increasing the rate of sequencing or simplifying the instrumentation), these ideal conditions cannot be achieved. Nonetheless, it is possible to practice numerous variations of the embodiment of FIGS. 4A–4E which still allow practical sequencing.

In general, there are three categories of nucleotides which can be employed in the practice of the embodiment of FIGS. 4A–4E. Native nucleotides are the preferred form, which provide the only opportunity for direct genomic sequencing and further eliminate possible sources of error, time and expense involved in the incorporation of non-native nucleotides into synthetic templates for sequencing. The second class of nucleotides are the fluorescent nucleotide analogs while the third class involves covalent attachment of fluorescent chromophores to nucleotides by means of linkers as explored by Jett et al., (U.S. Pat. No. 4,962,037). It must be recognized that in the latter two cases, it is necessary to first synthesize a copy of the DNA to be sequenced using an appropriate polymerase which is able to incorporate the nucleotide analogs or the dye-tagged nucleotides. Furthermore, it is necessary to employ an exonuclease which can cleave such synthetic templates containing nucleotide analogs or dye-tagged nucleotides.

In addition to methods which utilize only native nucleotides, nucleotide analogs, or dye-tagged nucleotides, there are four general possibilities for using combinations of these nucleotides: native nucleotides plus nucleotide analogs, native nucleotides plus dye-tagged nucleotides, nucleotide analogs plus dye-tagged nucleotides, and native nucleotides plus nucleotide analogs plus dye-tagged nucleotides. Within each of these four categories, all possible combinations are possible (e.g., 3 native plus 1 analog, 2 native plus 2 analogs, 1 native plus 3 analogs, etc.). The ability to combine various classes of nucleotides overcomes many of the difficulties encountered by others in attempting to incorporate dye-tagged nucleotides exclusively (1992 Harding and Keller, Trends in Biotechnology 10:55–57, which is incorporated herein by reference).

Further possibilities are provided by multi-pass sequencing, wherein the sequence is derived by sequencing the same strand multiple times. In each separate pass, information is obtained about one or more nucleotides by changing the operating parameters of the instrument and/or by employing different combinations of detectable nucleotides. The final sequence is obtained by combining information from such multiple passes. This method is further enhanced and extended by including the sequence of the complementary DNA strand. The exact combinations required for multi-pass sequencing will depend on whether: (a) the nucleotide can be uniquely discriminated from the other three nucleotides, (b) the nucleotide can be discriminated as either a purine or pyrimidine, (c) the nucleotide can be detected as a nucleotide, or (d) the nucleotide cannot be detected at all. It will be obvious to those skilled in the art that there are many combinations of these conditions for detection and discrimination which will allow sequencing to be carried out by the present invention. Several general examples are provided below for illustration, but they are not meant to limit the scope of possible combinations.

For example, if only one of each of the complementary pairs of the nucleotides can be discriminated (e.g., A and C) and their complements (e.g., G and T) can be detected as nucleotides but cannot be discriminated, then sequencing of both complementary strands will provide sufficient information to reconstruct the full sequence as illustrated below. This is independent of whether the nucleotides are native, analogs, dye-tagged or any combination thereof.

5'-ACGTTCAG-3'
3'-TGCAAGTC-5'

5'-ACXXXCAX-3'
3'-XXCAAXXC-5'

In a case where only one nucleotide can be discriminated and the other three are detectable as nucleotides, at least three and preferably four separate sequences will need to be combined to reconstruct the final sequence. The ability to discriminate a different nucleotide in each separate pass can be accomplished by adjusting the operating parameters of the nucleotide-containing matrix 71 and/or the operating parameters of the detection station 90 and/or by incorporating a different discriminateable nucleotide into a separate copy of the DNA template for each separate pass.

Even in cases where one or more nucleotides cannot be detected, it will be possible to sequence if the rate of cleavage of the exonuclease employed is sufficiently uniform. With a uniform generation of single nucleotides, the arrival time of the next nucleotide in the excitation region 100 can be predicted. Nucleotides which are not detectable will therefore show up as gaps in the sequence. Such gaps can then be filled in either by sequencing the complementary strand, if the nucleotide which is complementary to the undetectable nucleotide is itself detectable and discriminateable, or if the undetectable nucleotide can be made detectable and discriminateable in a subsequent pass by any of the methods indicated supra.

It is apparent that many modifications and variations of this invention as hereinabove set forth may be made without departing from the spirit and scope thereof. The specific embodiments described are given by way of example only and the invention is limited only by the terms of the appended claims. As used in the claims, the term "DNA" or "deoxyribonucleic acid" shall be construed as collectively including DNA containing native nucleotides, DNA containing one or more modified nucleotides (e.g., dye-tagged nucleotides containing a chemically or enzymatically modified base, sugar, and/or phosphate), DNA containing one or more nucleotide analogs, and combinations of the above unless expressly stated otherwise. As used in the claims, the term "nucleotide" shall be construed as collectively including native nucleotides, nucleotide analogs, modified nucleotides (e.g., dye-tagged nucleotides containing a chemically or enzymatically modified base, sugar and/or phosphate), and combinations of the above, unless stated otherwise.

What is claimed is:

1. A method of performing chemical, biochemical or biological reactions comprising the steps of providing in a thin liquid film at least first and second regions each containing a different chemical, biochemical or biological reagent, providing in the first region a particle to which the reagent of the first region is attached, forming in the first region an optical trap which traps said particle, using the optical trap to move the trapped particle through the liquid film to the second region; and interacting in the second region the reagent attached to the particle with the reagent of the second region wherein the liquid film is at least as thick as the diameter of the particle.

2. The method of claim 1 further comprising the step of moving the trapped particle from the second region to another area of the thin liquid film.

3. The method of claim 1 wherein the liquid film has a thickness that is approximately the same as the diameter of the particle that is trapped in the optical trap.

4. The method of claim 1 wherein the trapped particle is less than about 10 μm in size.

5. The method of claim 1 wherein the trapped particle is a bead less than about one μm in diameter.

6. The method of claim 1 for use in oligonucleotide synthesis wherein the first region contains a plurality of beads to each of which is attached a first nucleotide and a plurality of additional regions are provided on the thin liquid film, each region containing nucleotides of one type, or coupling reagents, or deblocking reagents, or capping reagents, or washing reagents, and the trapped particle is one such bead which is moved in a selected sequence from one region to another to synthesize a desired oligonucleotide.

7. The method of claim 1 for use in screening wherein the reagent from the first region is used to select from a variety of different molecules in the second region a molecule that binds to the reagent from the first region further comprising the step of using the optical trap to move the reagent and the molecule out of the second region and through the liquid film to a point where the molecule is recovered.

8. The method of claim 1 wherein at least one region is a droplet.

9. A method of performing chemical, biochemical or biological reactions on a surface comprising the steps of providing at least first and second discrete regions each containing a different chemical, biochemical or biological reagent, providing a thin liquid film which interconnects said at least first and second discrete regions, providing in at least said first discrete region a first particle to which the reagent of the first region is attached, moving the first particle through the liquid film to the second region, and interacting in the second region the reagent attached to the first particle with the reagent of the second region to perform a chemical, biochemical or biological reaction wherein the thin liquid film is at least as thick as the diameter of the first particle.

10. The method of claim 9 further comprising the step of moving the first particle from the second region to another area of the thin liquid film.

11. The method of claim 9 wherein the liquid film has a thickness that is approximately the same as the diameter of the first particle.

12. The method of claim 9 for use in oligonucleotide synthesis wherein the first region contains a plurality of beads to each of which is attached a first nucleotide and a plurality of additional regions are provided that are interconnected by the thin liquid film, each region containing nucleotides of one type, or coupling reagents, or capping reagents, or deblocking reagents, or washing reagents, and the trapped particle is one such bead which is moved in a selected sequence from one region to another to synthesize a desired oligonucleotide.

13. The method of claim 9 for use in screening wherein the reagent from the first region is used to select from a variety of different molecules in the second region, molecules that bind to the reagent from the first region, said method further comprising the step of moving the first particle and selected molecules out of the selected region and through the liquid film to a point where the selected molecules are recovered.

14. The method of claim 9 wherein at least one region is a droplet in the thin film.

15. A method of performing chemical, biochemical or biological reactions comprising the steps of providing in a thin liquid film at least first and second regions each containing a different chemical, biochemical or biological reagent, providing in the first region a particle to which the reagent of the first region is attached, forming in the first region an optical trap which traps said particle, using the optical trap to move the trapped particle through the liquid film to the second region; and interacting in the second region the reagent attached to the particle with the reagent of the second region wherein the liquid film has a thickness from 0.2 to 1.0 μm and the first and second regions are formed by depositing droplets of the reagents in the liquid film.

16. The method of claim 1 wherein the first and second regions are formed by depositing droplets of the reagents in the liquid film.

17. The method of claim 15 wherein the first and second regions are formed by depositing droplets of the reagents in the liquid film.

18. The method of claim 9 wherein the first particle is trapped in an optical trap and is moved by the optical trap through the liquid film.

* * * * *